US006500809B1

(12) United States Patent
Frazer

(10) Patent No.: US 6,500,809 B1
(45) Date of Patent: Dec. 31, 2002

(54) HYPERONCOTIC ARTIFICIAL CEREBROSPINAL FLUID AND METHOD OF TREATING NEURAL TISSUE EDEMA THEREWITH

(75) Inventor: Glenn Frazer, Wynewood, PA (US)

(73) Assignee: Neuron Therapeutics, Inc., Malvern, PA (US)

( * ) Notice: Subject to any disclaimer, the term of this patent is extended or adjusted under 35 U.S.C. 154(b) by 0 days.

(21) Appl. No.: 09/531,190

(22) Filed: Mar. 21, 2000

Related U.S. Application Data

(63) Continuation-in-part of application No. 09/440,038, filed on Nov. 12, 1999, now abandoned.

(51) Int. Cl.[7] .................... A61K 31/715; A61K 38/00; A61K 35/30

(52) U.S. Cl. .............................. 514/54; 514/9; 514/58; 514/59; 514/870; 424/570

(58) Field of Search .............................. 514/54, 9, 58, 514/59, 870; 424/570

(56) References Cited

U.S. PATENT DOCUMENTS

| | | | |
|---|---|---|---|
| 4,133,874 A | 1/1979 | Miller et al. | 424/38 |
| 4,378,797 A | 4/1983 | Osterholm | |
| 4,393,863 A | 7/1983 | Osterholm | |
| 4,425,334 A | 1/1984 | Hunt | 424/177 |
| 4,446,154 A | 5/1984 | Osterholm | 424/350 |
| 4,532,130 A | 7/1985 | Djordjevich et al. | 424/101 |
| 4,686,085 A | 8/1987 | Osterholm | |
| 4,776,991 A | 10/1988 | Farmer et al. | 264/4.3 |
| 4,840,617 A | 6/1989 | Osterholm | |
| 4,981,691 A | 1/1991 | Osterholm et al. | |
| 5,049,391 A | 9/1991 | Suzuki et al. | 424/450 |
| 5,128,452 A | 7/1992 | Hai et al. | 530/385 |
| 5,312,808 A | 5/1994 | Shorr et al. | 514/6 |
| 5,438,041 A | 8/1995 | Zheng et al. | 514/6 |
| 5,449,759 A | 9/1995 | Hoffman et al. | 530/385 |
| 5,563,254 A | 10/1996 | Hoffman et al. | 536/23.5 |
| 5,599,907 A | 2/1997 | Anderson et al. | 530/385 |
| 5,618,919 A | 4/1997 | Rausch et al. | 530/385 |
| 5,691,453 A | 11/1997 | Wertz et al. | 530/385 |
| 5,739,011 A | 4/1998 | Anderson et al. | 435/69.6 |
| 5,770,727 A | 6/1998 | Pliura et al. | 540/145 |
| 5,827,693 A | 10/1998 | De Angelo et al. | 435/69.6 |
| 5,952,470 A | 9/1999 | Light et al. | 538/385 |

OTHER PUBLICATIONS

Sundt et al. "Experiment cerebral infarction: modification by treatment with hemodiluting, hemoconcentration, and dehydrating agents" J. Neurosurg. 1967, 26(1), 46–56. AN 1967:74835.*

Bell, R.D. et al. (1991). "A Novel Treatment for Ischemic Intracranial Hypertension in Cats," *Stroke* 22(1):80–83.

Cordoba, J. et al. (May 1995). "Cerebral Edema and Intracranial Pressure Monitoring," *Liver Transplantation and Surgery* 1(3):187–194.

Hariri, R.J. et al. "Cerebral Edema," *Neurosurgery Clinics of North America* 5(4):687–706.

Williams, M.A. et al. (Dec. 1993). "Cerebrospinal Fluid Circulation, Cerebral Edema, and Intracranial Pressure," *Curr. Opin. Neurol.* 6(6):847–853.

Winslow, R.M. (1999). "New Transfusion Strategies: Red Cell Substitutes," *Ann. Rev. Med.* 50:337–353.

Cole, D.J. et al. (1993). "Focal Cerebral Ischemia in Rats: Effect of Hypervolemic Hemodilution with Diaspirin Cross–Linked Hemoglobin Versus Albumin on Brain Injury and Edema," *Anesthesiology* 78(2):335–342.

Hakamata, Y. et al. (1995). "Long–Term High–Colloid Oncotic Therapy for Ischemic Brain Edema in Gerbils," *Stroke* 26(11):2149–2153.

Miyasaka, Y. et al. (1983). "Albumin Oncotic Therapy for Patients with Increased Intra Cranial Pressure," *Neurol. Surg.* 11(9):947–954. (Abstract Only, 2 pages).

Önal, C. et al. (1997). "The Effect of Intraventricular Albumin in Experimental Brain Oedema," *Acta Neurochirurgica* 139(7):661–669.

* cited by examiner

*Primary Examiner*—Theodore J. Criares
*Assistant Examiner*—Jennifer Kim
(74) *Attorney, Agent, or Firm*—Dechert

(57) ABSTRACT

Neural tissue edema is treated by circulating a hyperoncotic artificial cerebrospinal fluid in the cerebrospinal fluid pathway in the vicinity of edematous tissue to cause the edematous tissue to be dehydrated due to an oncotic gradient between the hypertonic artificial cerebrospinal fluid and intracellular fluid and withdrawing the fluid from the pathway after it has been so circulated.

34 Claims, 5 Drawing Sheets

HYPERONCOTIC ARTIFICIAL CEREBROSPINAL FLUID AND METHOD OF TREATING NEURAL TISSUE EDEMA THEREWITH

RELATED APPLICATIONS

This is a continuation-in-part of U.S. patent application Ser. No. 09/440,038, filed Nov. 12, 1999, now abandoned.

TECHNICAL FIELD

This invention is in the field of neurosurgery. More particularly, it relates to hyperoncotic artificial cerebrospinal fluid and a method of treating neural tissue edema by circulating such fluid into contact with neural tissue via the cerebrospinal fluid pathway.

BACKGROUND OF THE INVENTION

The brain, spinal cord, and peripheral nerves are composed of neural tissue. However, only the brain and spinal cord are surrounded by cerebrospinal fluid (CSF). The most significant function of CSF is to cushion these organs against external traumatic forces applied to the head or body. Of similar importance is the contribution the cerebrospinal fluid pathway has made to the advancement of medical therapy by serving as a delivery system for drugs such as antibiotics, chemotherapy and anesthetic agents.

Cerebral edema is defined as an increase in the extravascular tissue water content of the brain. See Hariri, R. J., *Neurosurgery Clinics of North America*, October 1994, 5(4):687–706 and Williams, M. A. and Razumosky, A. Y., Current *Opinions in Neurology*, December 1993, 6(6):847–53. The main clinical significance of cerebral edema is raised intracranial pressure (ICP). Sustained and substantial elevation of ICP can cause brainstem herniation into the foramen magnum. Subsequent compression of the respiratory center in the brainstem leads to respiratory arrest and immediate death. Cerebral edema may be focal, as occurs in tumors, strokes, and abscesses or diffuse, as is often seen in hypoxic-ischemic injury (such as occurs from cardio-respiratory arrest and near drowning), and cranio-cerebral injuries. Cerebral edema can be diagnosed symptomatically in most instances, or by computed tomography (CT) brain scans which show hypodense areas of edema, small ventricles, obliteration of basal cisterns, and midline shift. Methods for monitoring ICP are also known. See Cordoba, J. and Blei, A. T., *Liver Transplantation and Surgery,* 1995 May, 1(3):187–94.

Once significant intracranial hypertension is identified, therapy must be prompt to prevent secondary cerebral ischemia. Treatments that have been used previously to treat elevated ICP include: hyperventilation; fluid restriction; osmotic diuresis; removal of cerebrospinal fluid; blood pressure control; and drug therapy (e.g., corticosteroids and barbiturates). In general, these therapeutic efforts are directed to: (1) control or manipulation of hydrostatic influences on the cerebrovascular system; (2) maintenance of the cerebrovascular permeability barrier, or (3) control or manipulation of osmotic and oncotic influences on trans-vascular fluid flux. However, these treatment modalities have not proved to be consistently effective and often create further metabolic and other systemic physiological problems.

Similar to cerebral edema, spinal cord edema results from increased fluid in the spinal tissue extravascular space. Spinal cord edema is a significant problem because it leads to spinal ischemia which can cause or potentiate a neurological deficit. Spinal cord edema may result from distortional forces or extrinsic compression. Distortional forces include traumatic flexion, extension, or rotation which shears neural and vascular elements. Extrinsic compression may be secondary to bony fragments (displaced fractures), hematoma, or tumor.

The spinal cord exists in a closed space environment where there is minimal room to expand. The cord is enclosed within the bony spine but is also directly covered by a relatively inelastic pial membrane. Due to this closed space environment, expansion of spinal cord tissue secondary to edema compresses spinal vessels. This limitation in blood flow causes the cord to become ischemic (secondary ischemia), initiating a cascade of events that creates more tissue edema (FIG. 1). Cerebral edema secondary to an ischemic episode or trauma is also affected by this process. Spinal cord edema can be diagnosed by clinical signs and symptoms and identified on magnetic resonance imaging (MRI) scans as high signal areas on T1- and T2-weighted images.

Many drugs have been investigated for the treatment of spinal cord injury, but results have been disappointing and their effect on spinal cord edema has not been widely studied. For example, methylprednisolone, a corticosteroid, has been advocated to improve functional (motor) recovery in traumatic spinal cord injury. However, after long-term follow-up, these clinical improvements are minimal, and patients are not found to significantly benefit from treatment when compared to control subjects. Morbid side effects such as GI bleeding and increased rates of wound infection have also been demonstrated in some studies.

The present invention concerns using oncotic influences variously to treat cerebral and spinal cord edema. Our artificial cerebrospinal fluid is used to counteract edema of any etiology and breaks the cycle of increasing neural tissue ischemia and edema. In the case of spinal cord edema, this treatment affords a wider therapeutic window.

Oncotic pressure is a manifestation of the difference in the colloid concentrations in fluids separated by a biological membrane. In the cerebral vasculature, the capillary walls act as a barrier between the plasma and interstitial fluid. The plasma contains significant amounts of proteins and other colloids that are too large to pass through the walls. The colloid osmotic pressure due to the presence of the colloids in the plasma (and relative lack thereof in extravascular fluid) is called the oncotic pressure and typically measures about 17–25 mm Hg. Oncotic pressure is one of the mechanisms the body uses to control fluid exchanges across biological membranes such as the capillary wall. Fluid is transported to the region of higher colloid concentration. Thus, in the brain and spinal cord, water is normally drawn into the capillaries from the surrounding interstitial fluid and tissue.

The effects of bolus infusions of hyperoncotic-hypertonic saline solution into the cerebral vasculature on ICP are reviewed by Hariri, R. J., supra. Such solutions (typically containing dextran as the oncotic agent) are reported to have reduced ICP in a rabbit model of cryogenic brain injury. In corresponding tests on human patients with severe head injury, the survival rates of patients in the group receiving hyperoncotic-hypertonic saline solution were greater than that for the control group. The investigators speculated that dehydration of brain tissue by the infused solution attenuated increased ICP.

Introduction of artificial cerebrospinal fluids in the CSF pathway to treat hypoxic and ischemic disorders in neurological tissue is known. For instance, U.S. Pat. Nos. 4,840,617; 4,686,085; 4,393,863; 4,378,797 and 4,981,691 describe using oxygenated aqueous emulsions of fluorocarbons containing electrolytes and nutrients in such a manner. U.S. Pat. No. 4,981,691 describes such an emulsion containing 1.8% by weight albumin (an oncotic agent). These patents do not, however, suggest circulating such fluids through the cerebrospinal fluid pathway to treat neural tissue edema.

Thus, as described above, osmotic-oncotic influences on neural tissue edema are well understood. Currently, no method has been devised for treating spinal cord edema. Further, various techniques, including the injection of hyperoncotic fluids into the cerebral vasculature, have been proposed for treating cerebral edema. Notwithstanding these prior techniques, new procedures for treating neural tissue edema are needed.

SUMMARY OF THE INVENTION

One aspect of the invention is a method for treating neural tissue edema, whether in intracranial or spinal disease, in a patient comprising:

a) introducing an artificial cerebrospinal fluid into the cerebrospinal fluid pathway at a first site; and b) withdrawing the fluid from the cerebrospinal fluid pathway at a second site selected to create circulation of said fluid in the vicinity of edematous neural tissue, said fluid containing a sufficient amount of an oncotic agent to cause the edematous neural tissue to be at least partially dehydrated.

Another aspect of the invention is an artificial cerebrospinal fluid for treating neural tissue edema, said fluid containing a sufficient amount of an oncotic agent to cause dehydration of edematous neural tissue contacted by the fluid.

MODES FOR CARRYING OUT THE INVENTION

The compositions and methods of the invention may be used to treat mammalian patients (e.g., sport or pet mammals such as dogs, cats and horses, and humans) who are experiencing neural tissue edema. The edema may be focal or diffuse. The cause of the edema is not important to the invention. In most instances, the edema will result from traumatic head or spine injury, tumors, abscesses, strokes, cardiac arrest, near drowning, or fulminant hepatic failure.

Figure 1:
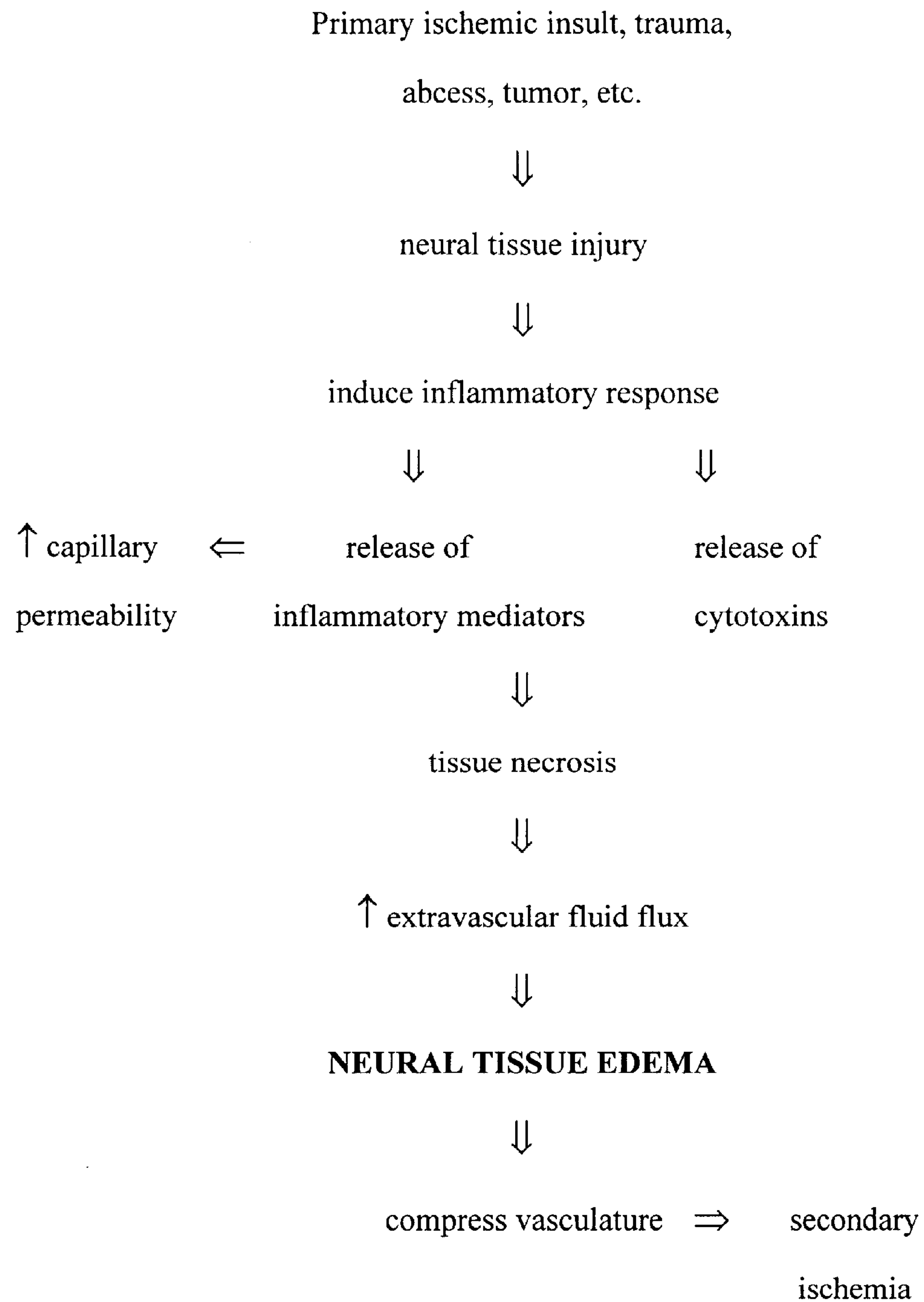
FIG. 1 is a diagram showing the futile cycle of edema and secondary ischemia that can develop in neural tissue after injury.

Avoidance of neural tissue edema is beneficial because it decreases secondary ischemia, which in turn prevents additional neural tissue injury and edema formation as illustrated in FIG. 1. Neural tissue injury caused by a primary ischemic event (stroke, cardiac arrest, near drowning), abcess, tumor, etc., will induce inflammatory cells to release cytotoxins and inflammatory mediators. Cytotoxins destroy living tissue (tissue necrosis). Inflammatory mediators enhance capillary wall permeability, thereby increasing neural tissue edema by increasing fluid flux into the extravascular space. Neural tissue edema (swelling of neural tissue) then compresses the vasculature supplying the tissue with oxygen, resulting in secondary ischemia. Secondary ischemia creates more neural tissue injury which stimulates the inflammatory response and the futile cycle of edema and secondary ischemia. Circulation of hyperoncotic CSF near areas of neural tissue edema would minimize edema formation by preventing fluid flux into the extravascular space. In FIG. 1, prevention of edema formation is clearly demonstrated (101).

Cerebral edema may be diagnosed or monitored directly by clinical observation or CT brain scan or indirectly by intracranial pressure measurements. Both non-invasive and invasive intracranial pressure measuring techniques are available. Invasive techniques typically involve placing an intracranial pressure transducer epidurally, subdurally, or intraparenchymally. In general, ICPs of less than 10 mm Hg are considered normal, with ICPs up to 15 mm Hg considered tolerable in humans. ICPs between 16 and 20 mm Hg lasting greater than thirty minutes should be treated promptly. Sustained elevation of ICP above 20 mm Hg can cause cerebral damage. Similarly, ICP elevation of any magnitude associated with pupillary dilatation and bradycardia typically requires urgent therapy.

Cerebral edema with elevated ICP and spinal cord edema associated with a focal neurologic deficit are treated according to the present invention with a hyperoncotic artificial cerebrospinal fluid. This fluid is comprised of components which, to the extent possible while maintaining its ability to induce fluid transport from neurological tissue, approach many of the physical and chemical characteristics of natural cerebrospinal fluid. Accordingly, the fluid preferably contains amounts of sodium, potassium, magnesium, calcium, chloride and bicarbonate ions in amounts approximating those in natural cerebrospinal fluid (see Table 1). Similarly, the fluid may contain amino acids, amino acid precursors, glucose and other moieties normally found in natural cerebrospinal fluid. Hyperoncocity is achieved by the presence of one or more oncotic agents in amounts suitable for removing water from the edematous tissue of concern. Examples of oncotic agents are the proteins naturally found in plasma (e.g. the albumin, globulin, and fibrinogen fractions), mixtures of such proteins derived from human blood plasma (commonly called plasma protein fraction), plasma extenders such as the dextrans (glucose polymers of preferably 40,000 to about 80,000 average molecular weight) and starch 2-hydroxyethyl ether (sold as Hespan by DuPont), dextrins (cyclodextrin), carboxymethyl cellulose, polyethylene glycol, glycogen, and pluronic acid.

The oncotic agent(s) will normally be present in the fluid in amounts sufficient to provide an oncotic pressure in the range of about 3 to 25 mm Hg., preferably 6 to 17 mm Hg. The oncotic agent(s) may be present in amounts ranging between 1.75% to 10% w/w, preferably about 2% to 8% w/w, depending, of course, upon the oncotic agent chosen.

Table 1 shows a set of ranges of the components in a typical artificial cerebrospinal fluid made without a specific oxygen-carrying component of the type discussed below.

TABLE 1

Composition of non-oxygen carrying artificial CSF

| COMPONENT | AMOUNT PER DOSE |
|---|---|
| Oncotic Agent | 200–450 mg/L |
| $Na^+$ | 135–145 mEq/L |
| $NaHCO_3$, | 20–25 mEq/L |
| Phosphorous | 1.2–2.0 mg/L |
| $K^+$ | 2.7–3.9 mEq/L |
| $Mg^{++}$ | 2.0–2.5 mEq/L |
| $Ca^{++}$ | 2.0–3.0 mEq/L |
| $Cl^-$ | 155–125 mEq/L |
| Glucose | 100–200 mg/L |

The fluid may also optionally contain one or more non-aqueous oxygen transfer compounds which are capable of selectively combining with oxygen and transferring the oxygen to neural tissue (see Table 2). Preferred oxygen transfer compounds are silicone polymers and fluorocarbon polymers, preferably perfluorocarbon polymers. Most preferably, bis-perfluorobutyl ethylene. The use of such oxygen transfer compounds in artificial cerebrospinal fluid is described in U.S. Pat. No. 4,981,691, which is incorporated by reference herein. When a nonaqueous oxygen transfer compound is included in the fluid, a suitable suspending/emulsifying agent may be added to facilitate dispersion of the oxygen transfer compound in the fluid and form an oxygenated aqueous emulsion of, e.g., a fluorocarbon. The inclusion of oxygen transfer compounds in the fluid is particularly desirable when it is necessary to treat hypoxic-ischemic conditions in the tissue as well as edema. See Bell, R. D. et al.: A Novel Treatment for Ischemic Intracranial Hypertension in Cats, *Stroke* 22(1):80–83, 1991.

TABLE 2

Composition of oxygenated artificial CSF

| COMPONENT | AMOUNT PER DOSE |
|---|---|
| Oxygen Carrying Component | 5-20% v/v |
| Oncotic Agent | 200–450 mg/L |
| $Na^+$ | 135–145 mEq/L |
| $NaHCO_3$, | 20–25 mEq/L |
| Phosphorous | 1.2–2.0 mg/L |
| $K^+$ | 2.7–3.9 mEq/L |
| $Mg^{++}$ | 2.0–2.5 mEq/L |
| $Ca^{++}$ | 2.0–3.0 mEq/L |
| $Cl^-$ | 115–125 mEq/L |
| Glucose | 100–200 mg/L |

A comprehensive review of oxygen transfer compounds undergoing investigation has recently been detailed. See Winslow, R. M.: New transfusion strategies: Red cell substitutes, *Annual Review of Medicine* 50:337–353, 1999.

In addition to perfluorocarbon-based products, cell-free hemoglobin and liposome encapsulated hemoglobin are also artificial oxygen carriers. Hemoglobin is a four-subunit protein that is the naturally occurring oxygen carrier in red blood cells.

Cell-free hemoglobin rapidly dissociates in the bloodstream, so artificial hemoglobins are chemically modified to prevent breadown. Artificial hemoglobins can be the product of surface modification, crosslinkage, or polymerization. The production and use of cell-free hemoglobin is detailed in U.S. Pat. Nos. 5,438,041; 5,770,727; 5,952,470; 5,691,453; 5,618,919; 5,599,907; 5,739,011; 5,563,254; 5,449,759; 5,128,452; 5,827,693, and 5,312,808 which are incorporated by reference. Hemoglobin can also be prevented from degradation by encapsulation within a protective barrier. Such is the case with liposome encapsulated hemoglobin, the production and use of which is presented in U.S. Pat. Nos. 5,049,391; 4,133,874; 4,776,991; 4,425,334, and 4,532,130. However, these oxygen transfer compounds are currently not components of an artificial cerebrospinal fluid, are not circulated in the cerebrospinal fluid space, and are not being used to decrease neural tissue edema. They are used to expand intravascular volume and deliver oxygen to tissues systemically in hypovolemic situations, as can occur during surgery, trauma, and septic shock. Artificial hyperoncotic CSF may contain one or more artificial hemoglobin compounds to deliver oxygen to edematous and/or ischemic neural tissue by circulation through the CSF pathway.

It is desirable to maintain the pH of the fluid at approximately that of natural cerebrospinal fluid (i.e., approximately 7.2 to 7.4). pH may be controlled by manipulating the amount of an ionic buffer such as dihydrogen phosphate, hydrogen phosphate, or bicarbonate in the fluid and/or the partial pressure of carbon dioxide. The temperature of the fluid will typically be at or below physiological temperature (i.e., about 37° C. in humans). It may be desirable to introduce the fluid at subphysiological temperatures (e.g., 3 to 36° C.) to induce hypothermic conditions in the tissue to reduce both edema and the effects of ischemia.

Figure 2:
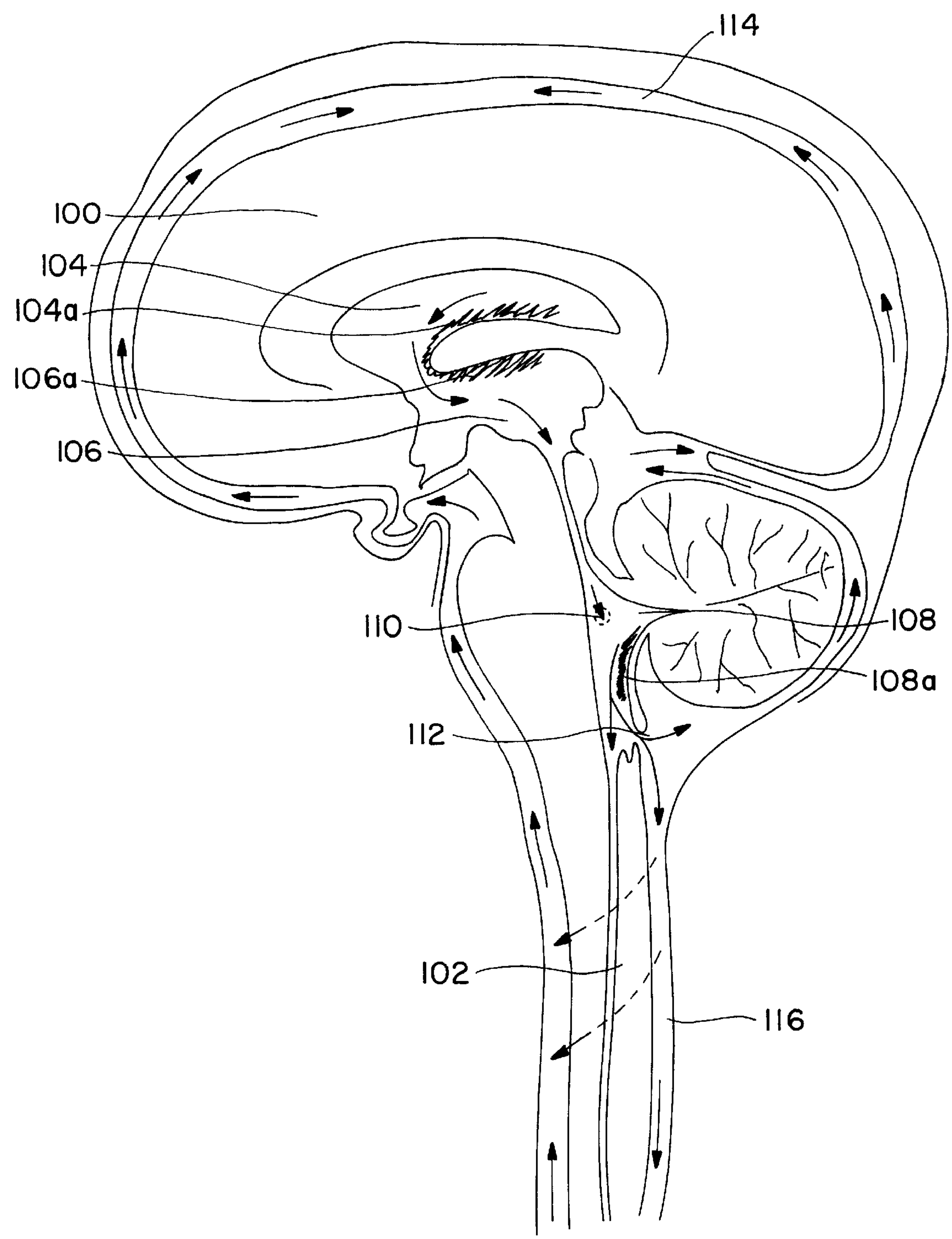
FIG. 2 is a lateral view of the cerebrospinal fluid pathway.

FIG. 2 shows the relationship of the brain (100) and spinal cord (102) to the pathway of cerebrospinal fluid flow. CSF is produced by the choroid plexus in the lateral (104*a*), 3rd (106*a*), and 4th (108*a*) ventricles at a rate of 500–750 ml/day. From the lateral ventricle (104), CSF travels through the 3rd ventricle (106) and 4th ventricle (108) to exit the foramen of Luschka (110) and foramen of Magendie (112) into the CSF space surrounding the brain (114) and spinal cord (116).

Figure 3:
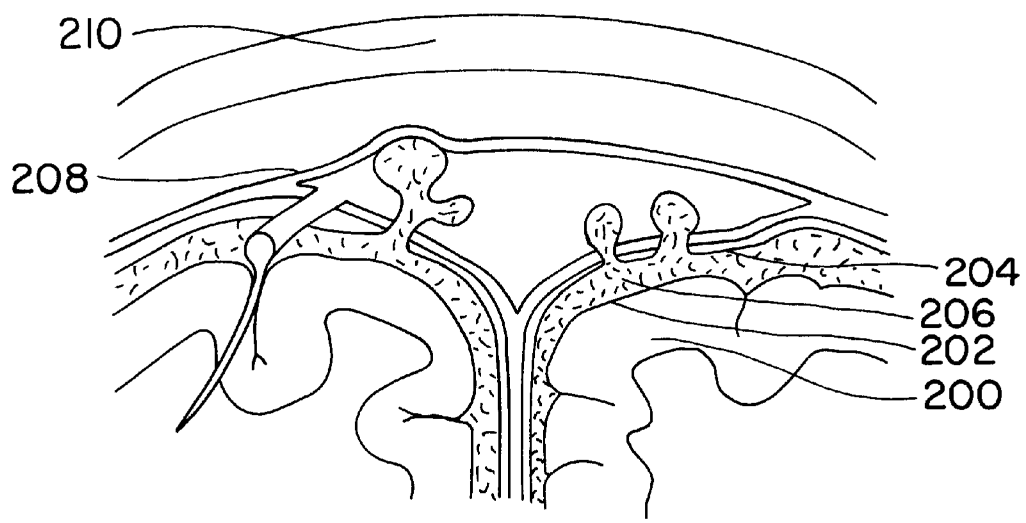
FIG. 3 is a coronal section of the superior frontal lobes of the brain showing the cerebrospinal fluid space and meninges.

The brain is enclosed within three membranes (meninges) which are shown in a coronal section of the superior frontal lobes in FIG. 3. Directly covering the brain (200) is the pia mater (202). The arachnoid (204) lies above the pia mater (202). Between the pia mater (202) and arachnoid (204) is the subarachoid space (206). CSF flows through the subarachnoid space (206). The dura mater (208) is a tough membrane that is located beneath the skull (210).

Figure 4:
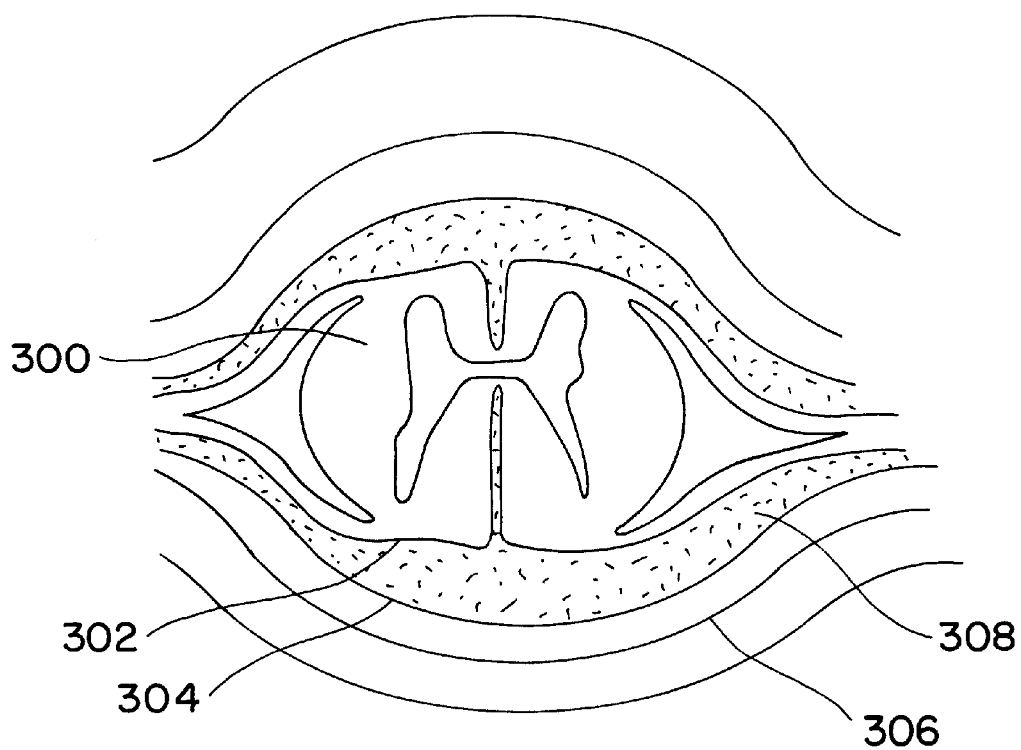
FIG. 4 is a transverse section of the vertebral column showing a superior view of the spinal cord and meninges.

FIG. 4 shows the spinal cord (300) to be enclosed within the same pia mater (302), arachnoid (304), and dura mater (306). The spinal subarachnoid space (308) directly communicates with the cerebral subarachnoid space (114). In accordance with the method in this invention, the hyperoncotic synthetic cerebrospinal fluid is circulated through the cerebrospinal fluid pathway by injecting it at a first point in the CSF pathway and withdrawing it from the pathway at a second point that is selected to create circulation of the fluid in the vicinity of the neural tissue to be dehydrated. By "dehydrate", we mean at least partial dehydration.

Figure 5:
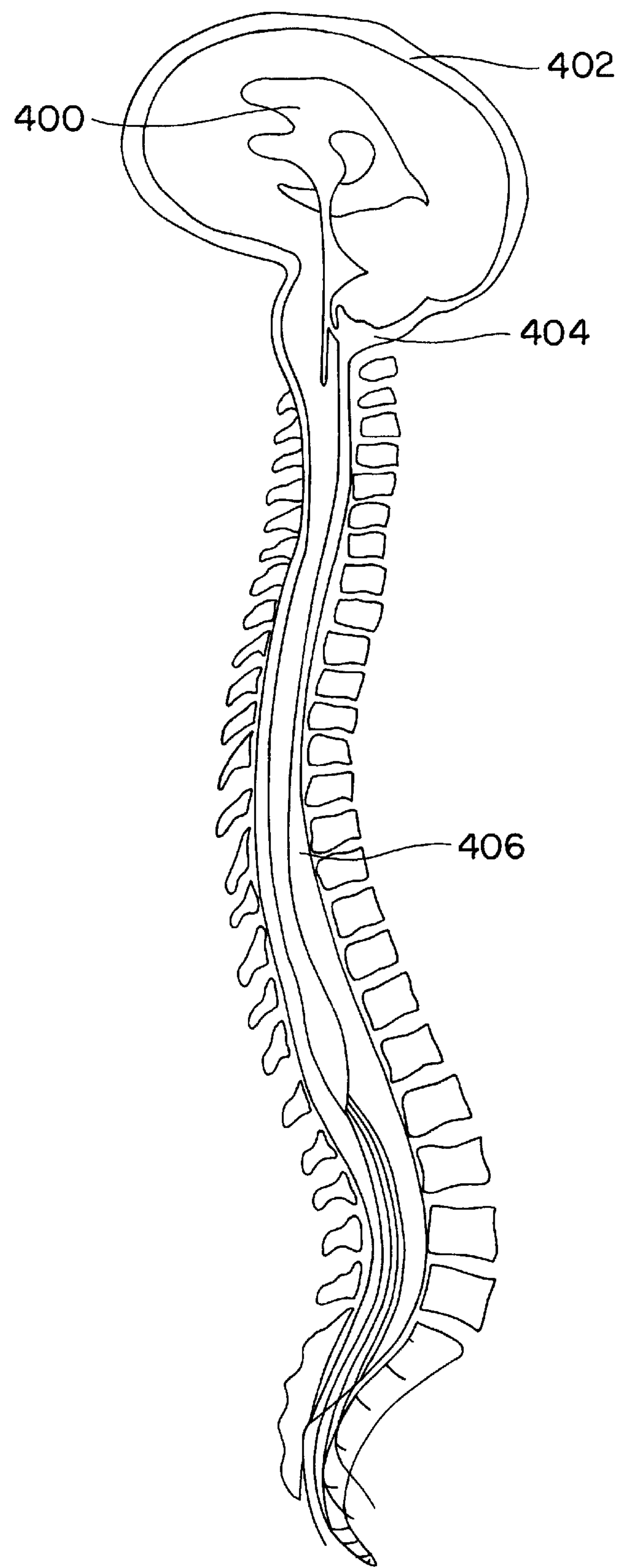
FIG. 5 shows sites of catheter placement for infusion or withdrawal of hyperoncotic cerebrospinal fluid.

FIG. 5 shows desirable sites of catheter placement for infusion or withdrawal of hyperoncotic artificial CSF. In the case of focal edema, it may be desirable to position the first and second points so that the fluid circulation is substantially localized in the vicinity of the edematous tissue. For instance, the fluid may be injected into the subarachnoid space at a first location and withdrawn from the subarachnoid space at a second location. For diffuse edema, the points are selected so that the fluid circulates in the vicinity of a significant portion of the neural tissue. For instance, the fluid may be injected into any intracranial CSF space such as the lateral ventricle (400), cerebral subarachnoid space (402), and cistema magna (404) or spinal subarachnoid space (406) and withdrawn from the cistema magna (404) or the spinal subarachnoid space (406).

Figure 6:
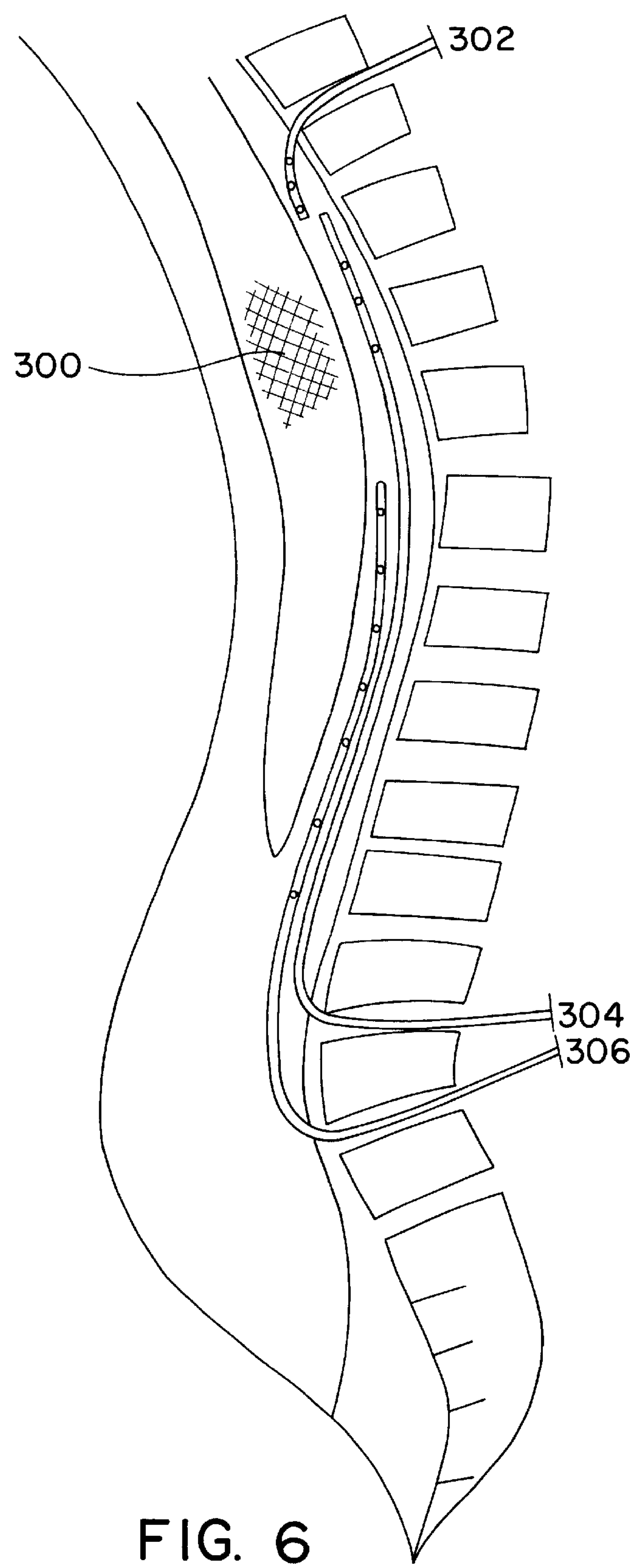
FIG. 6 shows spinal infusion and drainage catheters surrounding an area of spinal cord edema.

If isolated spinal cord edema is present, hyperoncotic cerebrospinal fluid circulation may be organized as depicted in FIG. 6. FIG. 6 shows two examples of hyperoncotic CSF circulation near an area of spinal cord edema (500). The pathway in one example uses an infusion catheter (502) that is placed proximal to the edematous tissue from the thoracic or thoracolumbar subarachnoid space as a first point, and drainage catheter (504) distal to the edema placed from the lumbar subarachnoid space as the second point. The infusion catheter (506) and drainage catheter (504) can also be threaded from lumbar spinous interspaces. Thus, first and second points may originate from the lumbar subarachnoid space. In all situations, due to the oncotic gradient between the hypertonic artificial cerebrospinal fluid and the interstitial fluid, water is drawn from the interstitial space of neural tissue into the cerebrospinal fluid pathway, thus dehydrating the tissue and reducing ICP.

The fluid may be circulated in a continuous, semi-continuous, intermittent, or pulsating manner. The flow rate of the hyperoncotic fluid will typically be in the range of about 1 to 100 ml/min, more usually 10 to 70 ml/min, with the actual flow desirably being titrated to maintain physiologic pressure in the intrathecal space. Circulation is typically continued until sufficient water has been removed from the tissue to correct the spinal cord edema or restore ICP to acceptable levels. The efficacy of the treatment may be monitored by monitoring ICP as described above or detecting improvement in neurologic deficits or edema on MRI.

The circulated fluid may be discarded or recirculated. If recirculated, appropriate measurements can be made to ensure that the withdrawn fluid remains biocompatible and efficacious and, if lacking in either respect, treated so that it meets standards before reintroducing it to the cerebrospinal fluid pathway. If recirculated, it may be treated to maintain or even to increase the oncotic pressure within the circulating fluid, by e.g., removing at least a portion of the water present by ultrafiltration or dialysis.

The following examples further illustrate the invention. The examples are not intended to limit the invention in any manner.

EXAMPLE 1

This Example shows the effect of subarachnoid perfusion with artificial cerebrospinal fluid (ACSF) both with and without albumin as an oncotic agent, on cerebral edema following cold injury.

Cerebral edema was induced in twenty anesthetized cats by the 60-second application of the end of a 0.88 $cm^2$ stainless-steel rod which had been cooled to the temperature of liquid nitrogen. Following injury, the animals were randomly assigned to either no treatment (n=6), or four hours of ventriculo-cisternal perfusion with ACSF, with albumin (n=6) or without albumin (n=8). The composition of the albumin-containing ACSF used in this Example is shown in Table 3.

TABLE 3

Composition of Albumin-containing ACSF

| Component | Amount, mL |
|---|---|
| NaCl, 0.9% | 385.0 |
| $NaHCO_3$, 1 meq/mL | 7.2 |
| KCl, 2 meq/mL | 0.6 |
| $CaCl_2$, 1.36 meq/mL | 0.9 |
| $MgSO_4$, 4.06 meq/mL | 0.3 |
| Dextrose, 10% | 4 |
| Sterile Water for Injection | 54.5 |
| Albumin, 25% | 17.5 |

The animals were sacrificed at 24 hours. Cerebral edema was indirectly assessed by tissue specific gravity determination at six bilateral sites. The injury model produced a significant difference in tissue specific gravity between the injured and the non-injured hemispheres at three sites in cortex and white matter adjacent to the injury and in the white matter immediately anterior to the injury site. Both treatments reduced the difference in specific gravity between the hemispheres as compared to control at these sites, but only in the albumin containing group was the effect significant ($p<0.05$, ANOVA with repeated measures).

| | Difference in Specific Gravity | | |
|---|---|---|---|
| Group | Adjacent Cortex | Adjacent White Matter | Anterior White Matter |
| Control | 0.00639 | 0.00869 | 0.00614 |
| S.D. | 0.00170 | 0.00113 | 0.00131 |
| ACSF + Albumin | 0.00418 | 0.00669 | 0.00405 |
| S.D. | 0.00170 | 0.00113 | 0.00131 |

In addition to the specific gravity determination after 24 hours, two volumetric MRI data acquisitions were performed at 12 hours following injury to obtain relative T1- and T2-weighted images to determine the volume of edematous tissue using segmental analysis. The data obtained was consistent with the specific gravity data. Reductions in edematous tissue volume were seen in the animals that received the albumin-containing ACSF.

It is clear that subarachnoid perfusion decreased tissue edema which could be secondary to enhanced clearance of mediators of edema (excitotoxins, cytokines, extravasated serum proteins).

EXAMPLE 2

The ACSF may also contain an oxygenated aqueous emulsion of a fluorocarbon and nutrients. The composition of the ACSF may be prepared according to the method of U.S. Pat. No. 4,981,691. The composition is shown in Table 4.

TABLE 4

Composition of Oxygenated Fluorocarbon-containing ACSF

| Component | Amount per Liter |
|---|---|
| Bis-perfluorobutylethylene (F44E) | 151.370 g |
| Lecithin | 10.500 g |
| NaCl | 6.674 g |

TABLE 4-continued

Composition of Oxygenated Fluorocarbon-containing ACSF

| Component | Amount per Liter |
|---|---|
| KCl | 0.199 g |
| $CaCl_2$-2 $H_2O$ | 0.198 g |
| $NaHCO_3$ | 1.359 g |
| $MgCl_2$-6 $H_2O$ | 0.037 g |
| $MgSO_4$-7 $H_2O$ | 0.288 g |
| $NaHPO_4$-7 $H_2O$ | 0.200 g |
| Glucose | 0.900 g |
| Albumin | 18.0 g |
| Glycine | 0.8 mg |
| L-lysine HCl | 3.7 mg |
| L-tryptophan | 2.0 mg |
| L-alanine | 2.3 mg |
| L-serine | 2.6 mg |
| L-threonine | 3.0 mg |
| L-arginine | 3.5 mg |
| L-leucine | 2.6 mg |
| L-valine | 2.3 mg |
| L-phenylalanine | 3.3 mg |
| L-tyrosine | 3.6 mg |
| L-histidine | 3.1 mg |
| L-methionine | 1.5 mg |
| L-isoleucine | 2.6 mg |
| α-ketoglutaric acid | 7.3 mg |
| Sterile Water for Injection | QS to 1000 mL |

What is claimed is:

1. A method of treating neural tissue edema in a patient comprising:

a) introducing a synthetic cerebrospinal fluid, which is not adapted to carry oxygen, into the cerebrospinal fluid pathway of the patient at a first point in the pathway; and b) withdraw the fluid from the pathway at a second point in the pathway selected to create circulation of the fluid in the vicinity of edematous tissue, said fluid containing a sufficient amount of an oncotic agent to cause the edematous tissue to be dehydrated.

2. The method of claim 1 where said neural tissue comprises brain tissue.

3. The method of claim 1 where said neural tissue comprises spinal cord tissue.

4. The method of claim 1 wherein the first point is in the intracranial cerebrospinal fluid space and the second point is in the cistema magna.

5. The method of claim 4 wherein said intracranial cerebrospinal fluid space comprises the lateral ventricles.

6. The method of claim 4 wherein said intracranial cerebrospinal fluid space comprises the cerebral subarachnoid space.

7. The method of claim 1 wherein the first point is in the intracranial cerebrospinal fluid space and the second point is in the spinal subarachnoid space.

8. The method of claim 7 wherein said intracranial cerebrospinal fluid space comprises the lateral ventricles.

9. The method of claim 7 wherein said intracranial cerebrospinal fluid space comprises the cerebral subarachnoid space.

10. The method of claim 7 wherein said intracranial cerebrospinal fluid space comprises the cisterna magna.

11. The method of claim 7 wherein said spinal subarachnoid space comprises the thoracic subarachnoid space.

12. The method of claim 7 wherein said spinal subarachnoid space comprises the lumbar subarachnoid space.

13. The method of claim 1 wherein the first point is in the spinal subarachnoid space and the second point is in the spinal subarachnoid space.

14. The method of claim 13 wherein said spinal subarachnoid space comprises the thoracic subarachnoid space.

15. The method of claim 13 wherein said spinal subarachnoid space comprises the lumbar subarachnoid space.

16. The method of claim 3 wherein said spinal cord tissue is edematous and isolated, the first point is in the thoracic subarachnoid space and the second point is in the lumbar subarachnoid space.

17. The method of claim 3 wherein said spinal cord tissue is edematous and isolated, the first and second points are in the lumbar subarachnoid space.

18. The method of claim 1 wherein the circulation is substantially continuous.

19. The method of claim 1 wherein the circulation is semi-continuous.

20. The method of claim 1 wherein the circulation is intermittent.

21. The method of claim 3 wherein the circulation has a fluid flow rate of 1 to 100 ml/min.

22. The method of claim 1 wherein the oncotic agent comprises a plasma protein or a plasma extender composition.

23. The method of claim 1 wherein the oncotic agent comprises albumin.

24. The method of claim 1 wherein the oncotic agent comprises a dextran.

25. The method of claim 1 wherein the amount of oncotic agent is sufficient to create an oncotic pressure in the range of 3 mm Hg to 25 mm Hg.

26. The method of claim 1 wherein the amount of oncotic agent is sufficient to create an oncotic pressure in the range of 10 mm Hg to 17 mm Hg.

27. The method of claim 1 further comprising the step of cooling the synthetic cerebrospinal fluid to a subphysiological temperature prior to introducing the fluid into the cerebrospinal fluid pathway of the patient.

28. The method of claim 1 further comprising the step of cooling the synthetic cerebrospinal fluid to a temperature between 3 and 36° C. prior to introducing the fluid into the cerebrospinal fluid pathway of the patient.

29. The method of claim 1 further comprising the step of recirculating the synthetic cerebrospinal fluid into the cerebrospinal fluid pathway of the patient after withdrawing the fluid from the pathway at a second point in the pathway.

30. The method of claim 29 further comprising the step of removing at least a portion of any water present in said withdrawn synthetic cerebrospinal fluid prior to returning said cerebrospinal fluid to the patient.

31. The method of claim 30 further comprising the step of ultrafiltering said recirculating synthetic cerebrospinal fluid to remove said water.

32. The method of claim 1 wherein said synthetic cerebrospinal fluid is essentially free of a component adapted to carry oxygen.

33. The method of claim 24 wherein said synthetic cerebrospinal fluid is essentially free of a component adapted to carry oxygen.

34. The method of claim 1 wherein said synthetic cerebrospinal fluid comprises sodium, potassium, magnesium, calcium chloride and bicarbonate ions in amounts approximating those in natural cerebral spinal fluid.

* * * * *